US011712430B2

(12) United States Patent
Magdassi et al.

(10) Patent No.: US 11,712,430 B2
(45) Date of Patent: Aug. 1, 2023

(54) FORMULATED CANNABIS OIL POWDER BY NANOEMULSIFICATION, METHODS OF PRODUCING AND USES THEREOF

(71) Applicant: KARNAK TECHNOLOGIES, LLC, New York, NY (US)

(72) Inventors: Shlomo Magdassi, Jerusalem (IL); Liraz Larush, Jerusalem (IL); Rafael Ezra, Tel-Aviv (IL)

(73) Assignee: Karnak Technologies, LLC, New York, NY (US)

( * ) Notice: Subject to any disclaimer, the term of this patent is extended or adjusted under 35 U.S.C. 154(b) by 0 days.

(21) Appl. No.: 16/958,341

(22) PCT Filed: Mar. 11, 2019

(86) PCT No.: PCT/IL2019/050268

§ 371 (c)(1),
(2) Date: Jun. 26, 2020

(87) PCT Pub. No.: WO2020/035850

PCT Pub. Date: Feb. 20, 2020

(65) Prior Publication Data

US 2021/0059975 A1 Mar. 4, 2021

(30) Foreign Application Priority Data

Aug. 13, 2018 (IL) ........................................ 261132

(51) Int. Cl.

| | |
|---|---|
| ***A61K 31/352*** | (2006.01) |
| ***A61K 9/00*** | (2006.01) |
| ***A61K 9/16*** | (2006.01) |
| ***A61K 31/05*** | (2006.01) |

(52) U.S. Cl.

CPC ............ *A61K 31/352* (2013.01); *A61K 9/006* (2013.01); *A61K 9/0053* (2013.01); *A61K 9/1641* (2013.01); *A61K 9/1652* (2013.01); *A61K 31/05* (2013.01)

(58) Field of Classification Search

CPC .... A61K 31/352; A61K 9/0053; A61K 9/006; A61K 9/1641; A61K 9/1652; A61K 31/05

See application file for complete search history.

(56) References Cited

U.S. PATENT DOCUMENTS

2016/0058866 A1 3/2016 Sekura et al.

FOREIGN PATENT DOCUMENTS

| | | |
|---|---|---|
| JP | 2013518097 | 5/2013 |
| WO | 2011092690 | 8/2011 |
| WO | 2013108254 | 7/2013 |
| WO | 2013108254 A1 | 7/2013 |
| WO | 2013172999 | 11/2013 |
| WO | 2013172999 A1 | 11/2013 |
| WO | 2015171445 | 11/2015 |
| WO | 2015171445 A1 | 11/2015 |
| WO | 2016135621 | 9/2016 |
| WO | 2016135621 A1 | 9/2016 |
| WO | 2016147186 | 9/2016 |
| WO | 2016147186 A1 | 9/2016 |
| WO | 2017180954 | 10/2017 |
| WO | 2017180954 A1 | 10/2017 |

OTHER PUBLICATIONS

Bei Liet et al., Lyophilization of Cationic Lipid-protamine-DNA (LPD) Complexes, Journal of Pharmaceutical Science, 2000, vol. 89:3, pp. 355-364.

Bei Li et al., Lyophilization of Cationic Lipid-Protamine-DNA (LPD) Complexes, Journal of Pharmaceutical Sciences, vol. 89, No. 3, Mar. 2000, pp. 355-364.

Lucia Martin-Banderas et al., Engineering of Δ9-Tetrahydrocannabinol Delivery Systems Based on Surface Modified-PLGA Nanoplatforms, Colloids and Surfaces B: Biointerfaces, vol. 123, 2014, pp. 114-122.

Matilde Duran-Lobato et al., Comparative Study of Chitosan- and PEG-Coated Lipid and PLGA Nanoparticles as Oral Delivery Systems for Cannabinoids, Journal of Nanopart Research, vol. 17:61, 2015, 17 pages.

*Primary Examiner* — Robert A Wax
*Assistant Examiner* — Olga V. Tcherkasskaya
(74) *Attorney, Agent, or Firm* — McAndrews, Held & Malloy, Ltd.

(57) ABSTRACT

The invention discloses particular water-dispersible solid formulation of a cannabinoid or a cannabis extract, wherein they are present in the form of a nanoemulsion, and upon dispersion in water said formulation produces nanoparticles (droplets of a submicron size) with an average size of up to about 500 nm. The present disclosure further relates to methods of making thereof, as well as therapeutic applications in humans for treating disorders and broader application for a range of medical conditions.

11 Claims, 8 Drawing Sheets

FORMULATED CANNABIS OIL POWDER BY NANOEMULSIFICATION, METHODS OF PRODUCING AND USES THEREOF

CROSS-REFERENCE TO RELATED APPLICATIONS

The present application is a National Phase Entry of PCT International Application No. PCT/IL2019/050268 which was filed on Mar. 11, 2019, which claims priority to Israel patent application 261132, filed Aug. 13, 2018, both of which are hereby incorporated by reference in their entireties.

TECHNOLOGICAL FIELD

The invention generally relates to formulations of cannabinoids, more specifically formulations as water-dispersible powders containing nanodroplets of a cannabinoid material, methods of producing thereof, as well as dosage forms and uses thereof for clinical purposes.

BACKGROUND

Medicinal value of cannabis is well documented. Cannabinoids, the active ingredients of cannabis, are produced in significantly higher amounts in resin-producing inflorescences of female cannabis plants. Various types of cannabis such as *C. sativa, C. indica, C. ruderalis* may produce more than 100 different types of cannabinoids in various concentrations and proportions. The two main cannabinoids, the tetrahydrocannabinol (THC) and cannabidiol (CBD), have been related to a number of biologically important activities in humans, and mammals in general.

The mammalian endocannabinoid system is a signal transduction system acting predominantly in the brain, and also in peripheral tissues. Several cannabinoid receptors have been identified so far, the most prominent are CB types 1 and 2 ($CB_1$ and $CB_2$). The endocannabinoid system has been implicated in maintenance of the normal mammalian homeostasis, including systems of movement control, pain, appetite, memory, immunity and inflammation, and others. This explains the high therapeutic potential of cannabis-based medicines, and exogenous cannabinoids, and their broad clinical applications.

Beneficial effects of cannabis have been revealed in a number of clinical conditions such as pain (pain in cancer, fibromyalgia related and neuropathic pain), inflammatory diseases (e.g. inflammatory bowel diseases, Crohn's disease, ulcerative colitis), posttraumatic stress disorder (PTSD), loss of appetite/anorexia, sleep disorders, multiple sclerosis (MS), epilepsy, autism, schizophrenia, and other disorders. In terms of broader biological effects, analgesic, antiemetic, antioxidative, neuroprotective and anti-inflammatory effects are only a few among various activities attributed to the two most studied cannabinoids THC and CBD.

Currently, medical cannabis is administered primarily through smoking or consumed orally in the form of oil, cookies, chocolates, etc. The majority of these products are not standardized with respect to cannabinoid compositions and doses.

A number of oral formulations of cannabinoids and cannabis-derived medicines are commercially available today by prescription for specific clinical indications. Marinol capsules containing dronabinol, a synthetic $\Delta^9$-THC isoform, in sesame oil, have been approved in a number of countries as an antiemetic for cancer patients under chemotherapy and patients with AIDS. Cesamet capsules with nabilone, a synthetic THC analog, have been approved as a Marinol substitute. More recent formulations Namisol tablets with pure THC and Arvisol tablets with pure CBD approved for Alzheimer's disease and chronic neural pain, and Sativex (nabiximols), an oral spray containing THC and CBD, for multiple sclerosis.

One general problem with pharmaceutical formulations of cannabinoids ensues from their highly lipophilic nature. Most of the existing cannabinoid- and cannabis-based formulations use relatively high concentrations of oil to achieve therapeutically effective concentrations of actives. Other major disadvantages, related to the aforementioned, is revealed in their poor bioavailability and high patient variability, as well as relatively short product life due to formulation instability.

Therefore, there is a clear incentive for the development of new and more progressive formulations of cannabinoids and cannabis-based preparations employing new technologies, such as nanoemulsions, microcapsules and other formulations.

GENERAL DESCRIPTION

The present invention provides solid formulations of cannabinoids or cannabis-based extracts in a form of readily water-dispersible fine powders or tablets containing oil droplets of predetermined sizes. One of the distinctive features of formulations of the invention is in their ability to recover, upon contact with water or a water-based environment, the same oil droplets, in substantially the same size. Specifically, the inventors have developed a solid-based delivery system derivable from an initial fine-tuned nanoemulsion that is tailored to contain lipophilic nanodroplets of a desired size. The conversion of the nanoemulsion to the solid-based delivery system, i.e., powder, maintains the integrity, content and size of the nanodroplets. Their integrity, content and size are further maintained when the solid-based delivery system is re-dispersed in water or when it comes into contact therewith.

This delivery system is not only unique, but even more so surprising as reconstitution of solid nanoemulsions typically results in a distortion of their form and size, usually in favor of larger spheres. Further studying the effect of various components and proportions thereof on the nanodroplets size, present in the initial nanoemulsion and the nanodroplets resulting from dispersing the powder in water, the inventors have found that this feature is highly exclusive and characteristic of a selection of compositions. In an oil model, the inventors demonstrated that in order to retain this feature the formulations should comprise at least one cryoprotectant such as sucrose, trehalose, or mannitol, at least one surfactant as ammonium glycyrrhizinate, pluronic F-127, F68, and optionally at least one carbohydrate such as maltodextrin and carboxymethyl cellulose (CMC). Certain combinations of these components and their ensuing effects on particle size are presently illustrated.

The inventors also demonstrated that particle size can be further modulated or controlled by selecting material combinations or by certain steps in the method of production of formulations of the invention, such that the size of the nanodroplets may be pre-tailored to be within 50 and 900 nm. This may be achieved, for example, by employing steps of lyophilization, homogenization and/or sonication to achieve the powder forms.

Further, the presently described solid formulations may be loaded with an large amounts of the lipophilic/oil fraction;

amounts that under some embodiments can be as high as 75% of the powder form or up to as much as 50% of the powder form (w/w). This feature is particularly important in view of the highly lipophilic nature of cannabinoids, their poor water-solubility and lability to thermal and photolytic degradation and oxidation, all making the design of cannabinoid formulations particularly challenging.

Liquid pharmaceutical formulations of cannabinoids are not always achievable. Despite the expected advantages (e.g., easy to swallow, uniform delivery and rapid onset), such formulations usually require relatively large volumes of solvents. With solid formulations, meant to overcome this disadvantage, dissolution of cannabinoids imposes a critical problem. Thus, the feature of high loading with respect to the lipophilic/oil fraction containing the cannabinoids, this without alcohols or other water-miscible solvents, or without any solubilizing agents, makes the cannabinoid formulations of the invention especially advantageous in terms delivery of therapeutically effectives doses of actives.

Still on this feature, the capability to modify or control loading of the oil fraction would be one way to control doses of actives in a formulation of a certain type, being it a cannabinoid-based (e.g., THC and/or CBD) or a cannabis-based formulation. Specifically for cannabis-based formulations, this provides a standardized pharmaceutical raw material with known concentrations of cannabis (unlike when dealing with inflorescences). In other words, the invention provides a solid homogeneous formulation of highly hydrophobic actives, in an administrable form, with relatively high load of actives, while being exempt from co-solvents such as alcohols. The formulations of the invention while being solid and compact are at the same time easily dispersible in water, with the actives retaining their properties in the oil phase, providing increased stability.

According to additional experiments, formulations of the invention remained stable for a period of 12 months or more. In this connection, it should be noted that the powder formulations of the invention can be further solidified or compressed into a solid form, such as a tablet and films, without affecting their stability and functionality.

The present invention further provides a method for producing such powder formulations. The methods of the invention have been presently exemplified using hemp oil and cannabis oils. Methods of the invention can be adapted to include one or more specific cannabinoids, synthetic or isolated from natural sources, and also complete or fractionated extracts of cannabis plants, in various proportions and combinations.

Another important objective of formulations of the invention is to maximize the potential of an increased bioavailability, especially for oral dosage forms. Achieving an effective oral delivery is essential for any successful therapeutic strategy, in terms of maximizing therapeutic effects, achieving stable and predictable drug plasma levels and pharmaco-dynamic effects, and as a consequence, increased patient compliance. Cannabinoids, however, have been proven particularly difficult to deal with due to their limited solubility in plasma and consequently limited bioavailability, and significant first pass effect. Thus there is still an unmet need for effective oral cannabinoid- and cannabis-based formulations, particularly in powder oral forms. The cannabinoid formulations of the invention due to their particular physical properties, being lipo-nanospheres of a particular particle (droplets) size, have a potential to overcome these limitations, in terms of increased dissolution or dispersion of actives, increased bioavailability and protection of actives from P-gp metabolism.

It is therefore yet another advantageous feature of formulations of the invention that they can be easily adapted to oral dosage forms such as tablets and sublingual tablets or capsules with various controlled doses of actives, i.e., cannabinoids or cannabis extracts, Such preparations can comprise additional therapeutic agents tailored for specific therapeutic indications which could benefit from cannabinoids and cannabis-based medicines. They can further comprise minerals, antioxidants, nutrients and vitamins in forms consumed directly with food.

The powder formulations can be further adapted for other administration methods, such as inhalation methods and devices, by using suitable pharmaceutical excipients. For example, in reconstituted forms the formulations of the invention can be further adapted as creams and aqueous dispersions for topical and transdermal administrations or generally as depositories.

Ultimately, the presently described formulations and dosage forms can be further improved by the addition of permeation enhancers to increase bioavailability, and controlled release agents in the form of a matrix or a coating using know in the art methods.

BRIEF DESCRIPTION OF FIGURES

The following figures illustrate certain advantageous features of the invention. It is stressed that the particulars shown are by way of example and for purposes of illustrative discussion of the embodiment of the invention.

(FIG. 1B) the dispersed powder (1% in water) with droplet size in the range of 70-130 nm (see Example 1).

DETAILED DESCRIPTION OF EMBODIMENTS

Figure 1A:
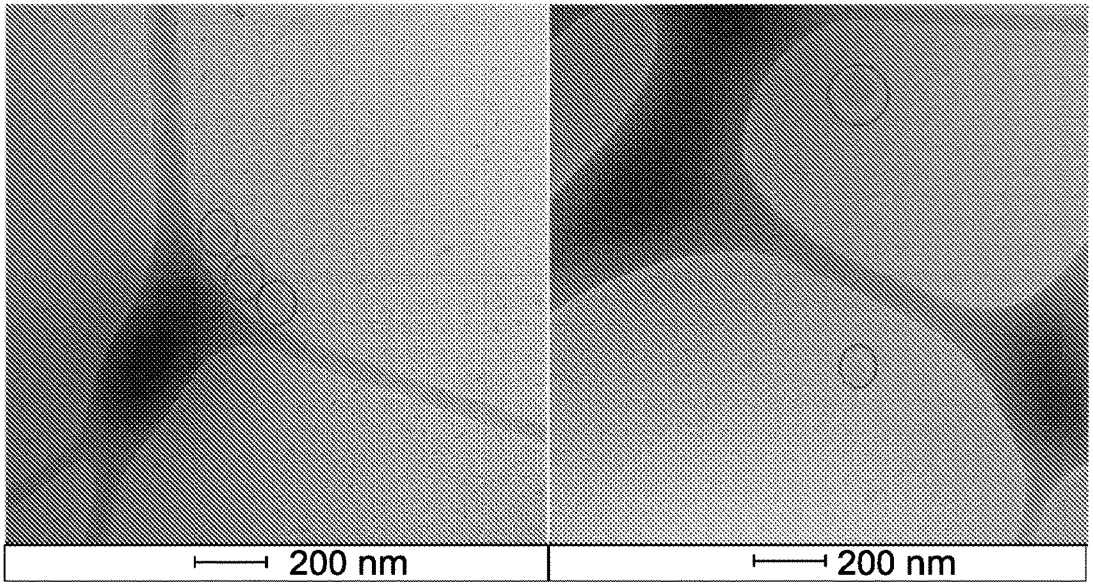
FIG. 1A-B shows Cryo TEM analysis of the formulation of the invention for (FIG. 1A) the nanoemulsion (10% in water) with droplet size in the range of 80-120 nm.

By describing specific embodiments of the invention it is not meant that this invention is limited to particular methods, and experimental conditions described, as such methods and conditions may vary. The terminology used herein is for the purpose of describing particular embodiments only and is not intended to be limiting, since the scope of the present invention will be limited only by the appended claims.

Thus, the invention first provides a water-dispersible powder comprising lipophilic nanospheres (or nanodroplets or lipo-nanospheres) having an averaged size between 50 and 900 nm, the nanospheres having an adsorbed layer of at least one solid surfactant and containing a cannabinoid material, wherein the at least one solid surfactant is selected from ammonium glycyrrhizinate, pluronic F-127 and pluronic F68; the powder further comprising at least one solid cryoprotectant selected from sucrose, trehalose and mannitol, and optionally at least one solid carbohydrate selected from maltodextrin and carboxymethyl cellulose (CMC); wherein the nanospheres structure and size is substantially maintained upon dissolution in a water containing environment.

As known in the art pluronic F-127 and pluronic F-68 are BASF ethylene oxide/propylene oxide block copolymers of known structures and molecular weights.

The powder of the invention is a solid form comprising a plurality of material nanospheres, each having a shell of at least one surfactant and containing the cannabinoid material. The expression "lipophilic nanospheres . . . having an adsorbed layer of at least one solid surfactant and containing a cannabinoid material" refers to the fact that these nanospheres, used interchangeably with nanodroplets or lipo-nanospheres, are material entities that are spherical or substantially spherical in shape, contain a cannabinoid material and surface-adsorbed by a film of the at least one surfactant. The nanospheres may have an adsorbed layer consisting of the at least one surfactant or have an adsorbed layer that comprises at least one surfactant as well as an amount of the other material components present in the powder.

The powder of the invention is derivable from a nanoemulsion that comprises a plurality of oil nanodroplets comprised of the cannabinoid material. In the nanoemulsion, the nanodroplets are of a size between 50 and 900 nm that is conserved in the solid powder. In fact, when the nanoemulsion is converted to a solid formulation, i.e., to the powder, the integrity, content and size of the nanodroplets is maintained.

The nanodroplets integrity, content and size are further conserved when the solid-based delivery system is re-dispersed in water or when it comes into contact therewith. The nanodroplets integrity, content and size are unaffected by acidic conditions and therefore powders of the invention may be delivered in vivo, ensuring safe and effective delivery of the nanodroplets cargo at pH values between 1 and 7.

Thus, for a variety of applications, e.g., medicinal applications and non-medicinal applications, powders with pre-tailored populations of oil droplets (nanospheres) of narrow size distributions may be prepared, to meet the target uses.

Powders with nanospheres having an averaged diameter as low as 50-100 nm as well as nanospheres having a submicron diameter, e.g., as high as 750-900 nm, are preparable by methods of the invention. Thus, the powders of the invention, as defined, may comprise nanospheres of a size between 50 and 900 nm, or between 50 and 100 nm, or between 50 and 150 nm, or between 50 and 200 nm, or between 50 and 250 nm, or between 50 and 300 nm, or between 50 and 350 nm, or between 50 and 400 nm, or between 50 and 450 nm, or between 50 and 500 nm, or between 50 and 550 nm, or between 50 and 600 nm, or between 50 and 650 nm, or between 50 and 700 nm, or between 50 and 750 nm, or between 50 and 800 nm, or between 50 and 850 nm, or between 100 and 150 nm, or between 100 and 200 nm, or between 100 and 250 nm, or between 100 and 300 nm, or between 100 and 350 nm, or between 100 and 400 nm, or between 100 and 500 nm, or between 100 and 550 nm, or between 100 and 600 nm, or between 100 and 650 nm, or between 100 and 700 nm, or between 100 and 750 nm, or between 100 and 800 nm, or between 100 and 850 nm, or between 150 and 900 nm, or between 150 and 800 nm, or between 150 and 700 nm, or between 150 and 600 nm, or between 150 and 500 nm, or between 150 and 400 nm, or between 150 and 300 nm, or between 150 and 200 nm, or between 200 and 900 nm, or between 200 and 800 nm, or between 200 and 700 nm, or between 200 and 600 nm, or between 200 and 500 nm, or between 200 and 400 nm, or between 200 and 300 nm, or between 250 and 900 nm, or between 250 and 800 nm, or between 250 and 700 nm, or between 250 and 600 nm, or between 250 and 500 nm, or between 250 and 400 nm.

In some embodiments, the nanospheres have an averaged diameter of between 200 and 400 nm, or between 250 and 400 nm, or between 250 and 350 nm, or between 200 and 500 nm, or between 250 and 500 nm.

In some embodiments, the nanospheres have an averaged diameter of between 100 and 400 nm, or between 150 and 400 nm, or between 150 and 350 nm, or between 100 and 500 nm, or between 150 and 500 nm.

In some embodiments, the nanospheres have an averaged diameter of between 200 and 250 nm, or between 250 and 300 nm, or between 300 and 350 nm, or between 350 and 400 nm, or between 400 and 450 nm or between 450 and 500 nm.

In some embodiments, the nanospheres have an averaged diameter of between 200 and 210 nm, or between 210 and 220 nm, or between 220 and 230 nm, or between 230 and 240 nm, or between 240 and 250 nm, or between 250 and 260 nm, or between 260 and 270 nm, or between 270 and 280 nm, or between 280 and 290 nm, or between 290 and 300 nm.

In some embodiments, the nanospheres have an averaged diameter of between 210 and 310 nm, or between 220 and 320 nm, or between 230 and 330 nm, or between 240 and 340 nm, or between 250 and 350 nm, or between 260 and 360 nm, or between 270 and 370 nm, or between 280 and 380 nm, or between 290 and 390 nm, or between 300 and 400 nm.

In some embodiments, the powder of the invention, upon dispersion in water, produces nanodroplets (spheres in the submicron scale) with an average size of between 50 and 900 nm, being an averaged size that is substantially identical. However, an increase or decrease in the size of the nanodroplets may be achieved upon dispersion. For example, a difference between the nanodroplets in the initial emulsion and the those in the dispersed medium may be tailored to about ±20-30 nm for emulsions with 10% dispersed fraction of the oil droplets and no higher than ±100 nm for emulsions with 30% dispersed fractions. The exact range can vary as indicated above, e.g., between 50-100 nm, 100-200 nm, 200-300 nm, 300-400 nm, 400-500 nm, and in certain embodiments more than 500 nm. The exact droplets size and size distribution can be controlled by changing the composition of the emulsion or features of the emulsion, such as phase fraction and surfactant concentrations and by changing the preparation parameters such as pressure and number of cycles in case high pressure homogenizer is used for preparing the emulsions.

Thus, the expression "nanospheres with a substantially same average size" supports the fact that the nanospheres present in the powder conserve their size upon reconstitution of the powder in water or a water containing environment.

The size is said to be "substantially the same", namely the average size is identical to that in the powder or is within ±10% of the original size.

In some embodiments, the powder of the invention comprises sucrose, trehalose or mannitol, a cannabinoid material and further ammonium glycyrrhizinate and maltodextrin.

In some embodiments, the powder comprises pluronic F-127 or pluronic F68, a cannabinoid material and further sucrose and maltodextrin.

In some embodiments, the powder comprises sucrose, ammonium glycyrrhizinate, maltodextrin, CMC and a cannabinoid material.

In some embodiments, the powder comprises ammonium glycyrrhizinate, Maltodextrin, sucrose and a cannabinoid material.

In some embodiments, the powder comprises mannitol, ammonium glycyrrhizinate, maltodextrin and a cannabinoid material.

In some embodiments, the powder comprises mannitol, ammonium glycyrrhizinate, maltodextrin, CMC and a cannabinoid material.

In some embodiments, the powder comprises trehalose, ammonium glycyrrhizinate, maltodextrin, CMC and a cannabinoid material.

In some embodiments, the powder comprises trehalose, ammonium glycyrrhizinate, maltodextrin and a cannabinoid material.

In some embodiments, the powder comprises mannitol, pluronic F-127, maltodextrin and a cannabinoid material.

In some embodiments, the powder comprises mannitol, pluronic F-127, maltodextrin, CMC and a cannabinoid material.

In some embodiments, the powder comprises trehalose, pluronic F-127, maltodextrin, CMC and a cannabinoid material.

In some embodiments, the powder comprises trehalose, pluronic F-127, maltodextrin and a cannabinoid material.

In some embodiments, the powder comprises mannitol, pluronic F-68, maltodextrin and a cannabinoid material.

In some embodiments, the powder comprises mannitol, pluronic F-68, maltodextrin, CMC and a cannabinoid material.

In some embodiments, the powder comprises trehalose, pluronic F-68, maltodextrin, CMC and a cannabinoid material.

In some embodiments, the powder comprises trehalose, pluronic F-68, maltodextrin and a cannabinoid material.

The at least one surfactant may be comprised in the powder in an amount ranging between about 1 and 10% (w/w), more specifically as high as 3%, 4%, 5%, 6%, 7%, 8%, 9%, 10% (w/w) surfactant.

In some embodiments, the amount of the surfactant may be less than 1% or more than 10%.

The amount of the at least one carbohydrate in the powder may be between 20 and 40% (w/w).

The amount of CMC, where used, may be about between 0.1 and 3% (w/w). In some embodiments, the mount of CMC is about 1%.

In some embodiments, powders of the invention comprise an amount of the cannabinoid material in the range of about 10-50% (w/w), more specifically in the range of 10-15%, 15-20%, 20-25%, 25-30%, 30-35%, 35-40%, 40-45%, 45-50% (w/w), or more.

The cannabinoid material may be a synthetic or natural cannabinoid(s), a cannabis extract(s) or a fraction thereof. In the broadest sense, this term denotes the entire class of chemical compounds, cannabinoid/cannabinoid agonists/cannabinoid-related compounds, acting with various affinities on the endogenous cannabinoid receptors (CB1 and CB2). This group of ligands include the endocannabinoids (produced naturally by humans and animals), phytocannabinoids (found in cannabis and some other plants), and synthetic cannabinoids (manufactured artificially).

Anorexia, emesis, pain, inflammation, multiple sclerosis, neurodegenerative disorders (such as Parkinson's disease, Huntington's disease, Tourette's syndrome, Alzheimer's disease), epilepsy, spasticity, autism, tuberculosis, inflammatory bowel diseases, including ulcerative colitis and Crohn's disease, irritable bowel syndrome, glaucoma, osteoporosis, schizophrenia, cardiovascular disorders, cancer, obesity, and metabolic syndrome-related disorders, fibromyalgia, graft versus host disease, constitute only a partial list of clinical conditions that are treatable by cannabinoid/cannabinoid agonists/cannabinoid-related compounds.

The term "cannabinoid material" further refers to the classical cannabinoids originating from or mimicking the natural cannabinoids in a cannabis plant. The main classes of the classical cannabinoids are shown in Table 1 below.

TABLE 1

| Representative examples of natural cannabinoids | |
|---|---|
| Type | Skeleton |
| Cannabigerol-type CBG | 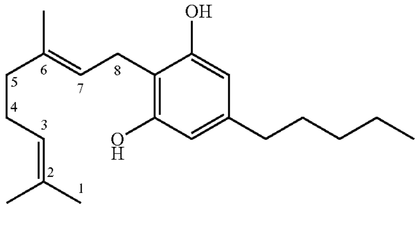 [SMILES: CCCCCc1cc(O)c(C/C=C(\C)CCC=C(C)C)c(O)c1] |

TABLE 1-continued
| Representative examples of natural cannabinoids | |
|---|---|
| Type | Skeleton |
| Cannabichromene-type CBC | 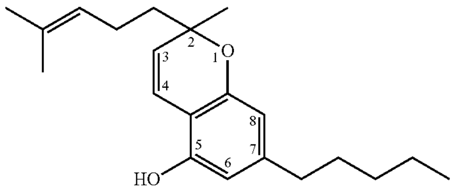 [SMILES: CCCCCc1cc(O)c2c(c1)OC(C)(CCC=C(C)C)C=C2] |
| Cannabidiol-type CBD | 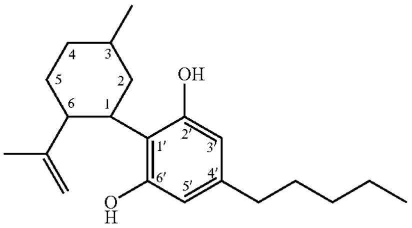 [SMILES: C=C(C)C1CCC(C)CC1c1c(O)cc(CCCCC)cc1O] |
| Tetrahydrocannabinol-and Cannabinol-type THC, CBN | 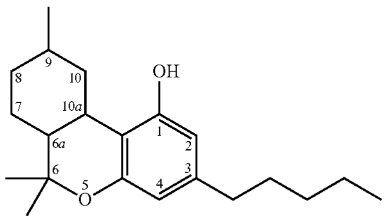 [SMILES: CCCCCc1cc(O)c2c(c1)OC(C)(C)C1CCC(C)CC21] |
| Cannabielsoin-type CBE | 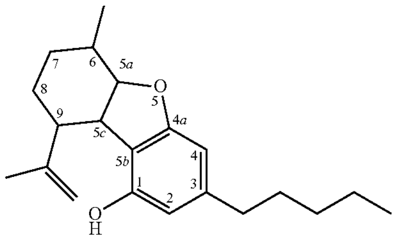 [SMILES: C=C(C)C1CCC(C)C2Oc3cc(CCCCC)cc(O)c3C12] |
| iso-Tetrahydrocannabinol-type iso-THC | 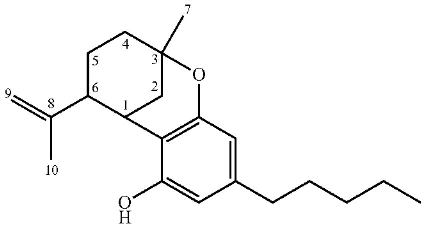 [SMILES: C=C(C)C1CCC2(C)CC1c1c(O)cc(CCCCC)cc1O2] |
| Cannabicyclol-type CBL | 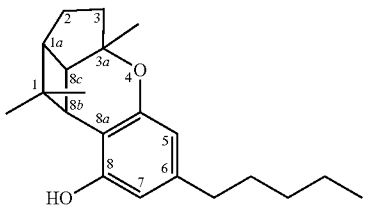 |

TABLE 1-continued

| Representative examples of natural cannabinoids | |
|---|---|
| Type | Skeleton |
| Cannabicitran-type CBT | 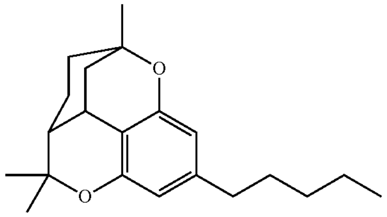 [SMILES: CCCCCc1cc2c3c(c1)OC(C)(C)C1CCC(C)(CC31)O2] |

In some embodiments, the powders of the invention comprise nanospheres with one or more cannabinoids belonging to one or more of the above classes.

In other embodiments, the powders of the invention comprise nanospheres with extract cannabis oils. Extract cannabis oils can be full extracts (FECO), one example of those is Rick Simpson Oil (RSO), or extracts enriched in specific cannabinoids (THC or CBD). Such extract oils can be obtained from *C. sativa, C. indica, C. ruderalis* strains, more potent preparations are obtained from female flowers.

It is yet another aspect of the invention to provide a method for producing a water-dispersible powder of the invention, the method comprising converting a nanoemulsion comprising at least one cannabinoid material to powder by a water-removal step, as disclosed herein, e.g., lyophilization, oven drying and spray-drying.

In some embodiments, the nanoemulsion comprising the at least one cannabinoid material comprises (a) an aqueous formulation comprising a cryoprotectant, a surfactant and optionally at least one carbohydrate, as defined herein; and (b) an oil comprising a synthetic or a natural cannabinoid, a cannabis extract or a fraction thereof.

In some embodiments, the method comprises:

(i) preparing or obtaining a nanoemulsion comprising (a) an aqueous formulation comprising a cryoprotectant, a surfactant and optionally at least one carbohydrate, as defined herein; and (b) an oil (e.g., an oil formulation) comprising a synthetic or a natural cannabinoid, a cannabis extract or a fraction thereof; and (ii) converting the nanoemulsion to a powder through removal of water, e.g., by lyophilization, oven drying or spray-drying.

In some embodiments, the method comprises preparing an aqueous phase comprising a cryoprotectant, a surfactant and optionally at least one carbohydrate, as defined above.

In some embodiments, the method comprises preparing an oil phase comprising a synthetic or a natural cannabinoid, a cannabis extract or a fraction thereof.

In some embodiments, the method comprises:

(i) preparing an aqueous phase comprising a cryoprotectant, a surfactant and optionally at least one carbohydrate, as defined above (ii) preparing an oil phase comprising a synthetic or a natural cannabinoid, a cannabis extract or a fraction thereof, (iii) preparing an emulsion by mixing (e.g., by a homogenizer) the oil phase and the aqueous phase, (iv) optionally sonicating/homogenizing the emulsion by e.g., a high pressure homogenizer and (v) converting the nanoemulsion to a powder, e.g., by lyophilization.

One of the important attributes of the method is that the nanoemulsion obtained, the powder formed, and the emulsion obtained upon dispersion of the powder in water produces nanospheres (nanodroplets) of substantially the same size, being a submicron size, and an average size as recited above.

In certain embodiments, the step of preparing the emulsion comprises high pressure homogenization of both phases for at least 1 to 10 runs, more specifically for at least 1, 2, 3, 4, 5, 6, 7, 8, 9, 10 runs or more.

In other embodiments, the step of preparing the emulsion can involve sonication for at least about 5-60 min, more specifically for at least about 5-10 min, 10-20 min, 20-30 min, 30-40 min, 40-50 min, 50-60 min or more.

In still other embodiments, the step of preparing the aqueous phase is carried out at room temperature.

It is another aspect of the invention to provide water-dispersible powders produced by a method of the invention, powders with the same physical and chemical properties in terms of particle size, type of constituents, actives and loading of actives as described above.

It should be noted that in certain embodiments the powders of the invention can be further solidified or compressed into solid forms. The solid forms can be tablets, capsules or films, as presently exemplified.

As powders of the invention retain their physical and chemical properties at room temperature for a period of at least 12 months or more, i.e., the powders of the invention remain stable for at least about 6 months, 9 months, 12 months or more at room temperature, they are easily convertible into pharmaceutical preparations of a variety of forms, suitable for a variety of administration modes and for use in a variety of medicinal applications.

It is thus another aspect of the invention to provide a pharmaceutical composition comprising water-dispersible powders, as above.

The compositions may be solid compositions or may be reconstituted compositions, in which case—in addition to the water-dispersible powders may further comprise a pharmaceutically acceptable buffer or liquid carrier.

In numerous embodiments, the pharmaceutical compositions of the invention comprise powders with synthetic or natural cannabinoids, cannabinoid combinations, cannabis extracts or fractions thereof.

In some embodiments, the composition of the invention comprise a synthetic or a natural cannabinoid which is one or more of tetrahydrocannabinol (THC), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), and a derivative, a precursor or an acid-form of any of the aforementioned.

All types of cannabinoids (those listed in Table 1 and others known as cannabinoids) are derived from cannabigerol-type compounds and differ mainly in the way this precursor is cyclized. The classical cannabinoids are derived from their respective 2-carboxylic acids (2-COOH, also denoted with -A) by decarboxylation (catalyzed by heat, light, or alkaline conditions). Of particular relevance to the invention are tetrahydrocannabinol and cannabidiol acid precursors, THC-A and CBD-A.

As has been mentioned, in numerous embodiments, the composition of the invention can comprise a full or partial extract in the form of a cannabis oil obtained from *C. sativa, C. indica, C. ruderalis* strains, flowers and other parts.

Oil extracts can be made using linseed oil, hemp oil, sesame oil, olive oil (the most common example), castor oil, chia seed oil, cotton oil, corn oil, coconut oil, sunflower oil, soybean oil, canola oil, etc. The linseed, castor and sesame oils are particularly advantageous as they contain alpha-linolenic acid, an essential nutrient.

Another advantage of cannabis-based compositions is in their added content of terpenes, sesquiterpenes, carotenes, flavonoids, being present in various combinations and proportions, and which contribute to absorption, activity and further to flavor-, odor-, and color-imparting properties, in the sense of being more user-friendly.

In numerous embodiments, compositions of the invention can comprise additional therapeutic agents. This feature is explained in detail below. In general terms, in view of the exceptionally board clinical applicability of cannabinoids and cannabis-based medicines there are a large number of applicable agents, e.g., antibiotic, anti-epileptic, anti-spastic, anti-inflammatory, analgesic and antipsychotic and others.

In numerous embodiments, compositions of the invention can further comprise antioxidants, minerals, nutrients, vitamins or combinations thereof, which can be consumed together with food or as food supplements. In this respect, compositions of the invention are particularly advantageous as many vitamins, such as vitamin E, have the same problems of solubility and bioavailability as the cannabinoids.

In terms of actives, compositions of the invention comprise up to about 75%, 60%, or 50% (w/w) actives, more specifically up to 10%, 15%, 20%, 25%, 30%, 35%, 40%, 45%, 50% (w/w) actives, and in certain embodiments even more. In this context, the term "active" refers to a cannabis oil or an oil form of the cannabinoid material.

In other numerous embodiments, compositions of the invention can further comprise antioxidants, absorption enhancers, color- and flavor-imparting agents, preservatives, stabilizers, salts, in various combinations. Various sweeteners, taste modifiers, antioxidants, preservatives which are well known in the art include taste modifiers such as artificial sweeteners, flavorings as strawberry and peppermint oil, for example, plant sweeteners, sugars, honey, Stevia, steviol, glycosides, citrate, acids, menthol, anise, eucalyptus oil, fennel, natural antimicrobial substances and natural antioxidant (e.g. extracts of murta, oregano, rosemary, borage), antioxidants such as vitamins E (tocopherol) and C and their derivatives, butylated hydroxyanisole (BHA), butylated hydroxytolune (BHT) recognized as GRAS, and sulfides; any sweetener allowed for oral administration such as sugar, glucose, sucralose, glycine, cyclamate, sucrose, saccharin, fructose, maltose, stevia extract, sodium saccharine; salts such as NaCl, $NaHCO_3$, $Na_2CO_3$, citrate, and others.

Other additives can be used, such as various solidifiers and viscosity modifiers, in various doses such as stearic acid, ascorbyle palmitate, palmitic acid, or hexadecanoic acid, polymers, magnesium stearate, cetyl alcohol, cetostearyl alcohols, stearyl alcohol; and specific viscosity enhancers such as polyvinyl alcohol (PVA), polyvinylpyrrolidone (PVP), sodium alginate, PG alginate, polyacrylic acids such as Carbopol, mucoadhesive polymers, Carbophils, celluloses, cellulose-ethers such as hydroxypropylmethyl cellulose (HPMC), hydroxypropyl cellulose (HPC), hydroxyethyl cellulose (HEC), hyaluronic acid (HA), alginic acid, xanthan gum, pectins, carrageenan.

In certain embodiments the compositions of the invention can further comprise a controlled release agent. This feature is explained in detail further below, in the context of oral dosage forms. In general terms, this feature here encompasses controlled and modifying release agents provided in the form of matrix and/or coating.

It should be noted that compositions of the invention are adaptable for any type of administration, as known in the medicinal or veterinary sciences. Powders as well as reconstituted formulations may be configured or engineered or adapted or selected or used for topical administration, enteral administration (e.g., including all systemic administration routes involving administration via the gastrointestinal tract), or parenteral administration (e.g., including all systemic administration routes, not involving administration via the gastrointestinal tract). Non-limiting administration routes effective for administration or powders or reconstituted formulations of the invention include oral, sublingual, mucosal, aerosol, inhalation, parenteral, subcutaneous, intravenous, intramuscular, interperitoneal, rectal and vaginal administrations.

As has been mentioned, it is another aspect of the invention to provide dosage forms for oral or sublingual administrations comprising the previously described compositions and powders.

The oral dosage forms of the invention can be generally characterized as comprising at least one synthetic or a natural cannabinoid, a cannabis extract or a fraction thereof.

In numerous embodiments, the oral dosage forms of the invention can comprise at least one synthetic or natural cannabinoid which is THC, CBD, CBN, CBG, CBC, CBL, CBV, THCV, CBDV, CBCV, CBGV, CBGM, as a derivative, a precursor or an acid-form.

In yet other embodiments, oral dosage forms of the invention can comprise a cannabis extract or a fraction obtained from a strain *C. sativa, C. indica, C. ruderalis* or a combination thereof.

As noted above, the oral dosage forms of the invention can further comprise additional therapeutic agents, minerals, nutrients, vitamins in various concentrations and combinations.

Of particular interest are oral dosage forms with a controlled release property. The term "controlled release" refers to a property or a modification enabling to achieve time dependent release, sustained release, prolonged release and also pulse release, i.e., delayed release of the drug. The term further relates to gastro-resistance, i.e., a property or a modification enabling to achieve pH-controlled drug release, gastrointestinal targeting, colon delivery, protection of acid-sensitive actives, protection of gastric mucosa from aggressive actives. In this sense, gastro-resistance is also targeted drug release. Gastro-resistant coatings and modifications are also known to improve storage stability.

Improved gastro-resistance and/or controlled release can be achieved by modification of and/or coating using various pharmacological technologies, such as use of poly(meth) acrylates or layering. A well know example of poly(meth) acrylate coating which has been widely used in the pharmacological industry to achieve targeted and controlled drug release is EUDRAGIT®. Another important feature of poly (meth)acrylate coating is protection from external influences (moisture) or taste/odor masking to increase patient compliance.

Certain solid oils can be added to facilitate controlled release, such as mono-, di- and triglyceride oils, in general, and trilaurin, tricaprin, tripalmitin, trimyristin, glyceryl, hydrogenated palm oil distearate, hydrogenated castor oil, hydrogenated vegetable oil, in particular.

In certain embodiments oral dosage forms of the invention can comprise matrix modifying/controlled release materials, which include, although not limited to, glycerides, waxes, fatty acids, methyl acrylate, methylmethacrylate, ethyl cellulose, poly(vinyl alcohol) (PVA), poly(vinyl pyrrolidone) (PVP), starch, polysaccharides, and others.

In other embodiments, oral dosage forms of the invention can be coated with hydroxypropyl methylcellulose, poly (meth)acrylates, methyl acrylate-methacrylic acid copolymers, cellulose acetate, polyvinyl acetate phthalate, and other types of coatings.

In numerous embodiments, the oral dosage forms of the invention can be provided in the form of a tablet or a capsule, both being the most popular and convenient methods of oral drug delivery.

With respect to capsules, optionally a capsule can be coated with a gastro-resistant coating using GRAS-based materials.

In further embodiments these dosage forms can use a secondary package, such as a blister (PVC/PVDC—Alufoil), a bottle, an aluminum pouch, others.

It should be appreciated that one of the particular features of the presently described dosage forms is their stability at room temperature.

In yet another aspect, the above described powders, composition and dosage form of the invention can be applied for the treatment and alleviation of a number of disease and medical conditions, specifically those wherein beneficial effects of cannabinoids or cannabis-based medicines have been previously demonstrated. In other words, the invention provides a range of therapeutic methods for treating diseases or medical conditions related to beneficial effects of cannabinoids or cannabis, by application of presently described powders, pharmaceutical compositions or dosage forms.

As has been noted, the therapeutic methods of the invention can be applied to a wide range of human conditions, including inflammatory, neurological, psychiatric disorders, malignancies and further immune, metabolic disorders, nutritional deficiencies, infectious diseases, and types of gastrointestinal disorders, cardiovascular disorders, and various types of pain, including chronic and neuropathic pain.

Considering the present level of knowledge regarding clinical applications of cannabinoids in young and elderly patients, it is projected that the presently described preparations and methods can be applied to, although not limited to depression, sleeping disorders, eating disorders, cancer, multiple sclerosis, graft versus host disease (GVHD), Parkinson's, epilepsy, autism, tuberculosis, ulcerative colitis, morbus Crohn, inflammatory bowel disorder (IBD), irritable bowel syndrome (IBS), appetite stimulant, appetite depressant, obesity, nausea, neuropathic pain, anxiety, Alzheimer's disease, amyotrophic lateral sclerosis (ALS), gastrointestinal disorders, hypertension, incontinence, pruritus, arthritis, arthrosis, rheumatic inflammation, insomnia, mycosis, local and/or chronic pain, inflammation, attention deficit and hyperactivity disorder (ADDH), vomiting, atopic dermatitis, fibromyalgia, AIDS, mood disorders, erectile dysfunction, premature ejaculation, nutritional deficiency.

It should be appreciated that the presently described preparations and methods are applicable to subjects that are infants, adolescents or adults.

It should also be noted that powders, compositions and dosage forms of the invention are applied in therapeutically effects amounts. In general terms, a "therapeutically effective amount" (also a pharmacologically or a pharmaceutically or a physiologically effective amount) denotes an amount of the cannabinoid material needed to achieve the anticipated or desired physiological response. The precise amount is dependent on numerous factors, e.g. the type of agent, activity and intended use (e.g. number of doses per day), which can be determined by known in the art technologies. It is understood that the effective amount can be the result of empirical and/or individualized (case-by-case) determination on the part of the treating health care professional and/or individual.

In numerous embodiments, the therapeutic preparations of the invention, the powders, compositions and dosage forms, can comprise therapeutically effective amounts of cannabinoid actives in the range of at least about 1-10 mg, 10-50 mg, 50-100 mg, 100-150 mg, 150-200 mg, 200-250 mg, and more.

In further embodiments, the therapeutically effective amounts of cannabinoid actives can be in the range of at least about 50-100 mg, 100-150 mg, 150-200 mg, 200-250 mg, 250-300 mg, 300-350 mg, 350-400 mg, 400-450 mg or 450-500 mg.

Larger therapeutic doses can involve multiple daily administrations.

The terms "treating", "treatment" or "therapy" or any lingual variation thereof, refer equally to curative therapy and ameliorating therapy. The terms encompass any approach for obtaining beneficial or desired therapeutic effects, which may be established clinically by means of physiological, metabolic or biochemical parameters. Beneficial or desired clinical results include, but are not limited to, alleviation of symptoms, diminishment of extent of disease, stabilization of symptoms, delay or slowing of progression, amelioration or palliation of a condition or a symptom, and remission (whether partial or total). The term "palliation" encompasses herein undesirable manifestations of a physiological condition or a symptom which are lessened and/or a progression which is slowed or lengthened, as compared to the same but untreated condition.

Still further, in certain embodiments, preparations and methods of the invention involve combination therapies, administered simultaneously or in succession with other methods and drugs (also therapeutic agents).

Therapeutic agents that are relevant can be, although not limited to General Drug Categories, classified by the FDA according to their clinical effects and applicability to common human disorders: analgesics, antacids, antianxiety drugs, antiarrhythmics, antibacterials, antibiotics, antimicotics, anticoagulants and thrombolytics, anticonvulsants, antidepressants, antidiarrheals, antiemetics, antifungals, antihistamines, antihypertensives, anti-inflammatories, antineoplastics, antipsychotics, antipyretics, antivirals, barbiturates, beta-blockers, bronchodilators, cold cures, cholesterol lowering drugs, corticosteroids, cough suppressants, cytotoxics, decongestants, diuretics, expectorant, hormones, hypoglycemics, immune-suppressive, laxatives, muscle relaxants, sedatives, sex hormones, sleeping drugs, tranquilizer and vitamin supplements, such as omega fatty acids, omega-3-fatty acids, EPA, DHA, ALA.

In terms of therapeutic effects, an improvement as a result of treatment is identified if there is at least about 5% improvement, or 10% improvement, or at least 25%, or at least 50%, or at least 75%, or at least 100% improvement or more. An improvement herein can be interpreted in the sense of individual improvement as well as population improvement.

The term "about" in all its appearances in the text denotes up to a ±10% deviation from the specified values and/or ranges, more specifically, up to ±1%, ±2%, ±3%, ±4%, ±5%, ±6%, ±7%, ±8%, ±9% or ±10% deviation therefrom.

Unless defined otherwise, all technical and scientific terms used herein have the same meaning as commonly understood by one of ordinary skill in the art to which this invention belongs. It should be understood that any methods and materials similar or equivalent to those described herein can be used in the practice or testing of the present invention. Some embodiments of the invention will be now described by way of examples with reference to accompanying figures.

Thus, in summary—the invention provides, inter alia, the following:

A water-dispersible powder comprising lipophilic nanospheres (submicron nanodroplets) containing a cannabinoid material and further comprising:

at least one cryoprotectant selected from sucrose, trehalose, mannitol, at least one surfactant selected from ammonium glycyrrhizinate, pluronic F-127, pluronic F68, and optionally at least one carbohydrate selected from maltodextrin and carboxymethyl cellulose (CMC).

In some embodiments, upon dispersion in water the powder produces nanodroplets with a substantially same average size.

In some embodiments, the powder comprises sucrose, trehalose or mannitol and further comprising ammonium glycyrrhizinate and maltodextrin.

In some embodiments, the powder comprises pluronic F-127 or pluronic F68, and further comprising sucrose and maltodextrin.

In some embodiments, the powder comprises sucrose, ammonium glycyrrhizinate, maltodextrin and CMC.

Other embodiments are recited hereinabove.

In some embodiments, wherein the cannabinoid material comprises at least one synthetic or a natural cannabinoid, a cannabis extract or a fraction thereof.

In some embodiments, the powder wherein the concentration of a surfactant is in the range of about 3-10% (w/w).

In some embodiments, wherein the fraction of lipophilic nanodroplets is in the range of about 10-50% (w/w).

In some embodiments, the powder is in a solidified or compressed solid form. The invention further provides a method for producing a water-dispersible powder, the method comprising converting to a powder by lyophilization an emulsion of an oil phase and an aqueous phase; the aqueous phase comprising a cryoprotectant, a surfactant and optionally at least one carbohydrate, as defined herein, the oil phase comprising a synthetic or a natural cannabinoid, a cannabis extract or a fraction thereof.

In some embodiments, the method comprises:

(i) preparing an initial emulsion by an oil phase into an aqueous phase; the aqueous phase comprising a cryoprotectant, a surfactant and optionally at least one carbohydrate, as defined herein, the oil phase comprising a synthetic or a natural cannabinoid, a cannabis extract or a fraction thereof, (ii) preparing a final emulsion by sonicating or homogenizing the initial emulsion; and (iii) converting the nanoemulsion to powder by lyophilization.

In some embodiments, the method comprises:

(i) preparing an aqueous phase comprising a cryoprotectant, a surfactant and optionally at least one carbohydrate, as defined herein, (ii) preparing an oil phase comprising a synthetic or a natural cannabinoid, a cannabis extract or a fraction thereof, (iii) preparing an initial emulsion by adding the oil phase into the aqueous phase during homogenization, (iv) preparing a final emulsion by sonicating or homogenizing the initial emulsion, and (v) converting the nanoemulsion to powder by lyophilization.

In some embodiments, the nanoemulsion obtained in (iv) and the powder in (v), upon dispersion in water, produce nanospheres (nanodroplets) with a substantially identical average size.

In some embodiments, the step of preparing the initial emulsion in (iii) further comprises high pressure homogenization for at least 1 to 10 runs or more.

In some embodiments, the step of preparing the final emulsion in (iv) involves sonication for at least about 5-60 min.

In some embodiments, the step of preparing the aqueous phase in (i) is carried out at room temperature.

Further provided is a water-dispersible powder produced by a method of the invention.

In some embodiments, the oil phase is in the range of about 10-50% (w/w).

In some embodiments, the powder is in a solidified or compressed solid form.

EXAMPLES

Example 1

Method of Preparation of the Formulation (an Oil Model)

A. Preparation of the Nanoemulsion

Stage I Aqueous Phase 0.25 gr ammonium glycyrrhizinate, (Sigma, 50531-50G, cas: 53956-04-0), 2 gr Maltodextrin, (Sigma, 419699-500G, cas: 9050-36-6), 2 gr sucrose, (Sigma, 59378-500G, cas: 57-50-1) and 14.3 gr triple distilled water (TDW) were mixed using a magnetic stirrer for 10 min at 35-40° C. until a complete dissolution and acquisition of an aqueous solution.

Stage II Oil Phase 0.5 gr olive oil (commercial) was added to the solution of Stage I.

Stage III Initial Emulsion 0.5 gr of the olive oil/hemp oil was added to the aqueous phase drop ways in the course of homogenization by high shear homogenizer (ULTRA TORAX, IKA T25 digital, 10,200 rpm) for at least 5 min.

Stage IV Final Emulsion

The homogenized emulsion was sonicated in an ice bath (Ultrasonic cell crusher SKL-750, SYCLON, Probe 1.1 cm diameter as probe no. 10) for 10 min under the conditions of Amplitude: 90%, ON: 2 sec, OFF: 1 sec.

B. Conversion of the Nanoemulsion to Powder

Stage V Lyophilization

1. The nanoemulsion was transferred to a glass vail and the vail was frozen in a bath of liquid nitrogen for 5 minutes.

2. The vail was lyophilized at absolute pressure of <1 mbar for 48 h (Labconco freezone 2.5).

The resultant powder, being a dry fine powder, was stored in closed glass vials.

Stage VI Dispersion in Water

The powder was dispersed (0.1-1 wt %) in TDW. The samples were vortexed for 1-2 min to obtain a translucent emulsion.

Droplet size: Droplet size of the O/W nanoemulsion was estimated at Z Average: 160 nm peak 1: 99 nm, 56%; peak 2: 281 nm, 44%, polydispersity index (Pdi): 0.191 (measured by dynamic light scattering (DLS); and after dispersion in water at Z Average: 173 nm peak 1: 94 nm, 43.3%; peak 2: 274 nm, 53.6%; peak 3: 4943 nm, 3.1%, Pdi: 0.227.

Stability: The powder containing 10.5% w/w of olive remained stable after at least 9 weeks of observation.

Compositions of the nanoemulsion and powder are presented in Tables 2 and 3.

TABLE 2

Composition of the nanoemulsion

| Ingredients | % w/w |
|---|---|
| olive oil | 2.6246 |
| Maltodextrin | 10.4986 |
| Sucrose | 10.4986 |
| Ammonium glycyrrhizinate | 1.3123 |
| TDW | 75.065 |

TABLE 3

Composition of the oil powder

| Ingredients | % w/w |
|---|---|
| olive oil | 10.5263 |
| Maltodextrin | 42.10526 |
| Sucrose | 42.10526 |
| Ammonium glycyrrhizinate | 5.26315 |

Figure 1B:
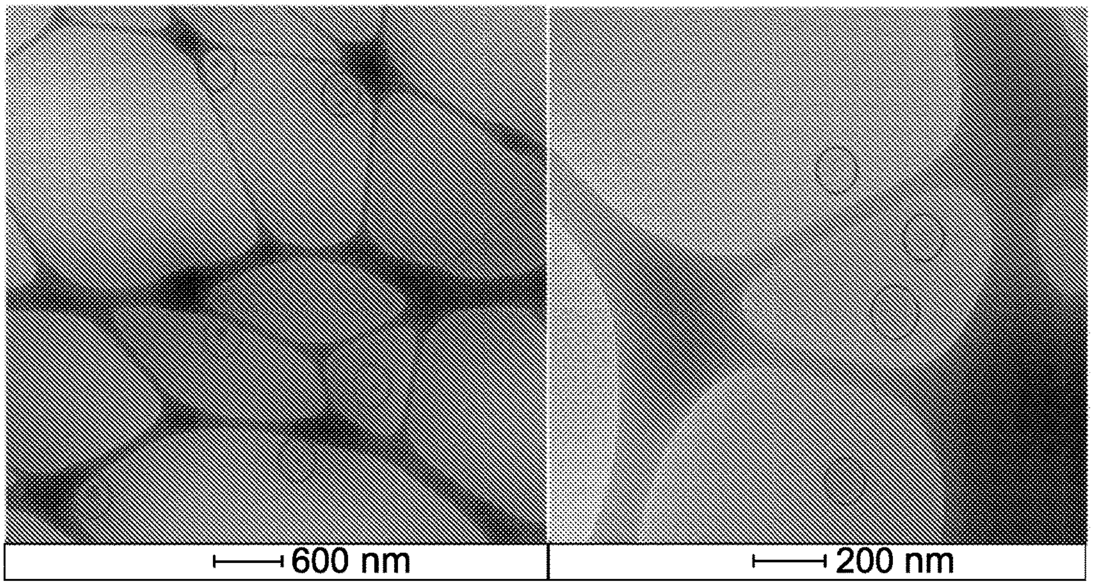

Characterization: Cryo TEM analysis was conducted for the emulsion (10% in water) and for the dispersed powder (1% in water). The images are presented in FIG. 1.

Example 2

Proof-of-Concept Using Hemp Oil

The same experiments were conducted using 10% hemp oil out of 90% olive oil fraction, and 100% oil fraction of hemp oil. Sonication, lyophilization and dispersion conditions were as in Example 1. Droplet size of the O/W nanoemulsion was estimated at the following values:

For the 10% hemp oil: Z Average: 173.6 nm peak 1: 192.9 nm, 100%, Pdi: 0.213; and after dispersion in water at Z Average: 191.6 nm peak 1: 194 nm, 100%, Pdi: 0.290.

For the 100% hemp oil: Z Average: 163.3 nm peak 1: 184.7 nm, 93.2%; peak 2: 4956 nm, 1.1%; peak 3: 38 nm, 5.7%, Pdi: 0.169; and after dispersion in water at Z Average: 166 nm peak 1: 99.30 nm, 55.4%; peak 2: 287.3 nm, 44.6%, Pdi: 0.221.

Example 3

Applicable Cryoprotectants

The same experiments were conducted using trehalose or mannitol instead of sucrose as cryoprotectant, under the same conditions in terms of sonication, lyophilization and dispersion as in Example 1. Droplet size of the O/W nanoemulsion was estimated at the following values:

For trehalose: Z Average: 157.5 nm peak 1: 169.3 nm, 100%; polydispersity index (Pdi): 0.191; and after dispersion in water at Z Average: 171.6 nm peak 1: 163.6 nm, 98.9%; peak 2: 4703 nm, 1.1%, Pdi: 0.276.

For mannitol: Z Average: 142.4 nm peak 1: 145.4 nm, 94%; peak 2: 30 nm, 6%; polydispersity index (Pdi): 0.169; and after dispersion in water at Z Average: 167.7 nm peak 1: 180.9 nm, 89.2%; peak 2: 36 nm, 10.8%; Pdi: 0.212.

Example 4

Applicable Surfactants—Permeation Enhancers

The same experiments were conducted with pluronic F-127 and pluronic F-68, (Polyoxyethylene-polyoxypropylene block copolymer) instead of ammonium glycyrrhizinate as surfactant under the same conditions as in Example 1. Droplet size of the O/W nanoemulsion was estimated at the following values:

For pluronic F-127: Z Average: 149.7 nm peak 1: 141.1 nm, 100%, Pdi: 0.183; and after dispersion in water at Z Average: 199.8 nm peak 1: 218 nm, 100%, Pdi: 0.149.

For pluronic F-68: Z Average: 145.7 nm peak 1: 154.8 nm, 100%, Pdi: 0.161; and after dispersion in water at Z Average: 241.7 nm peak 1: 259.4 nm, 99.1%; peak 2: 5362 nm, 0.9%, Pdi: 0.263.

Example 5

Effect of Surfactant Concentration on Droplet Size

Figure 2:
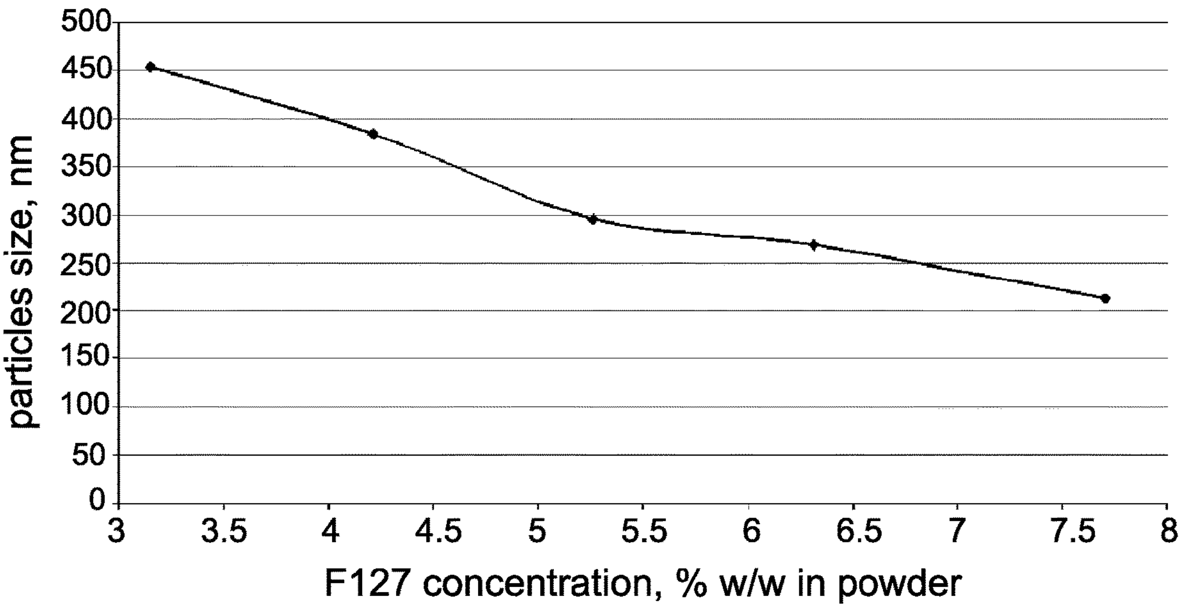
FIG. 2 shows the effect of surfactant concentration (between 3.2-7.7% w/w) on droplet size of a formulation of the invention (in the range of 251-450 nm) (see Example 5).

The nanoemulsions were prepared with different surfactant concentrations in the range of 3.15-7.7% w/w in the powder. For example, 0.15-0.35 gr pluronic F-127, 1.9-2.1 gr Maltodextrin, 2 gr sucrose, and 14.3 gr TDW were mixed using a magnetic stirrer for 10 min at 35-40° C. until a complete dissolution, all other components, and homogenization and sonication parameters remained the same. The effect on the droplet (particle) size is demonstrated in FIG. 2.

Example 6

Effect of Sonication Time on Droplet Size

Figure 3:
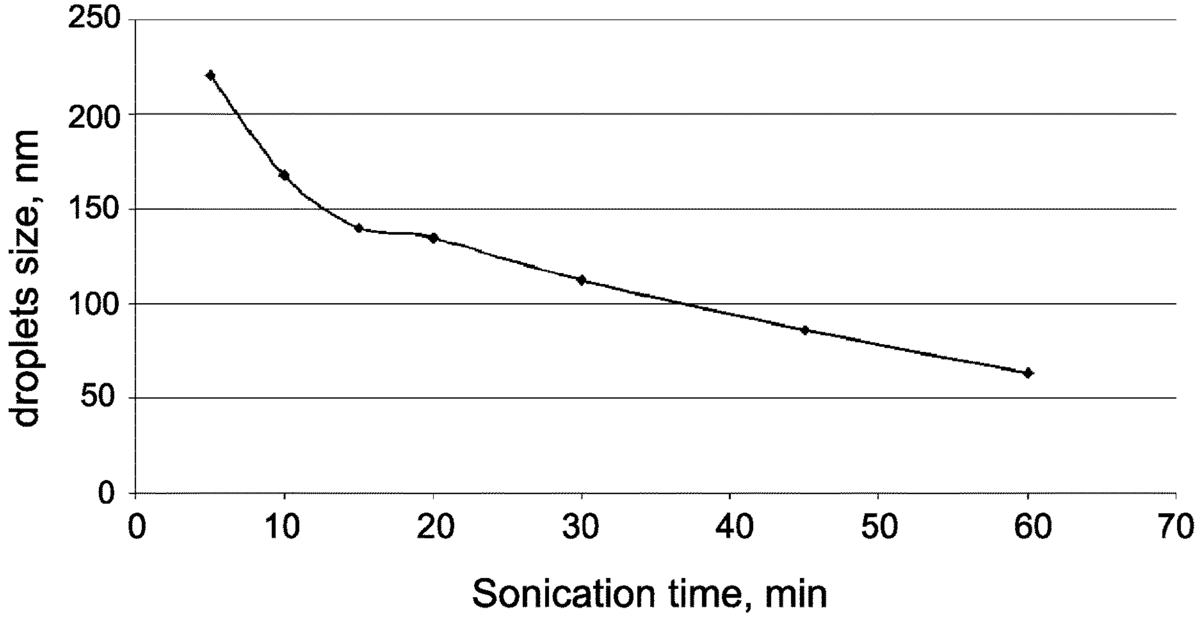
FIG. 3 shows the effect of sonication time (between 5 to 60 min) on the droplet size of the formulation (in the range of 60-220 nm) (see Example 6).

The nanoemulsions were prepared with 0.25 gr ammonium glycyrrhizinate as surfactant. The emulsions were sonicated as in stage IV, Example 1, for the duration of 5 to 60 min, all other components and homogenization parameters remained the same. The effect on the droplet (particle) size is demonstrated in FIG. 3.

Example 7

The Effect of High Pressure (HP) Homogenizer

The following formulation was prepared: 0.5 gr Pluronic F127, 4 gr Maltodextrin, 4 gr sucrose, and 28.6 gr TDW were mixed using a magnetic stirrer for 10 min at RT until a complete dissolution. In the next stage, 1 gr of the hemp oil was added to the aqueous phase drop ways during homogenization by high shear homogenizer as in stage III, Example 1, this stage was repeated 4 times to obtain a sufficient amount of product for the homogenization step.

Figure 4:
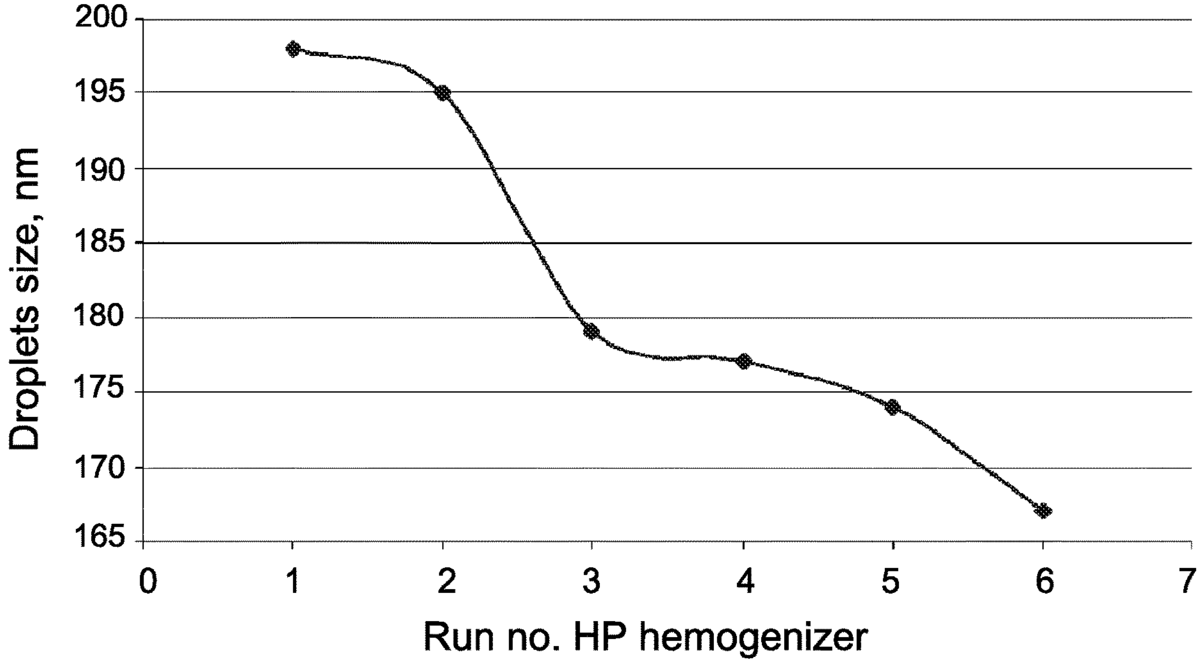
FIG. 4 shows the effect of high pressure homogenization (between 1-6 runs) on droplet size of the formulation (in the range of 167-198 nm) (see Example 7).

The final emulsion was prepared by HP homogenizer wherein 100 gr of the obtained emulsions were subjected to homogenization for 1 to 6 runs (cycles). The results are demonstrated in FIG. 4. Droplet size of the O/W nanoemulsion was estimated at the following values:

For 1 homogenization run: Z Average: 182 nm peak 1: 198 nm, 97.5%; peak 2: 4976 nm, 2.5%, Pdi: 0.151.

For 6 homogenization runs: Z Average: 157 nm peak 1: 167 nm, 100%, Pdi: 0.122.

The lyophilization and dispersion steps were as in stage V-VI, Example 1. Droplet size after dispersion in water was estimated at Z Average: 210 nm peak 1: 2064 nm, 100%, Pdi: 0.235.

Example 8

The Effect of Hemp Oil Concentration

Figure 5:
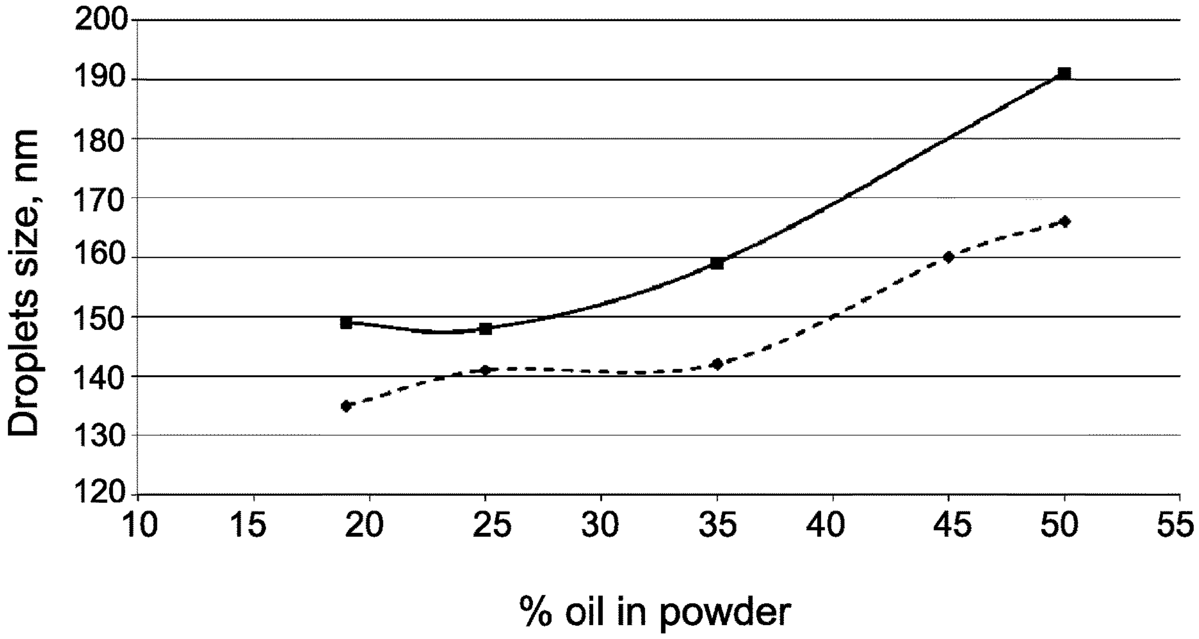
FIG. 5 shows the effect of hemp oil concentration (between 19-50% w/w) on droplets size of the nanoemulsion (dashed) and dispersed powder (solid) with droplets in the range of 130-190 nm (see Example 8).

The following formulations were prepared: 0.3 gr ammonium glycyrrhizinate, 1.95 gr Maltodextrin, 2 gr sucrose, and 14.3 gr TDW were mixed as in Example 1. In the next stage, 1-4.25 gr of hemp oil (19-50% oil in powder) was added to the aqueous phase drop ways during homogenization as in stage III and sonicated as in stage IV, Example 1. The results are demonstrated in FIG. 5.

Example 9

Preparation of High-Load Formulations

A high load formulation (50% hemp oil) was prepared as follows: 2.1 gr ammonium glycyrrhizinate, 13.65 gr Maltodextrin, 14 gr sucrose, and 100.1 gr TDW were mixed as in Example 8. In the next stage, 29.75 gr of hemp oil (50% oil in the powder) was added to the aqueous phase drop ways during homogenization by high shear homogenizer as in Example 8. The final emulsion was prepared by HP homogenizer as in Example 7. Droplet size of the O/W nanoemulsion was estimated at the following values:

For 6 homogenization runs: Z Average: 182 nm peak 1: 107 nm, 33%, peak 2: 308 nm, 67%, Pdi: 0.177.

For 10 homogenization runs: Z Average: 176 nm peak 1: 202 nm, 98, peak 2: 4956 nm, 2%, Pdi: 0.146.

For 15 homogenization runs: Z Average: 175 nm peak 1: 201 nm, 100%, Pdi: 0.137.

Droplet size after dispersion in water was estimated at Z Average: 181 nm, peak 1: 114 nm, 41%, peak 2: 303 nm, 53%, peak 3: 1763 nm, 6%, Pdi: 0.193.

Example 10

Use of Carboxymethyl Cellulose (CMC)

The following formulation was prepared: 0.3 gr ammonium glycyrrhizinate, 1.95 gr Maltodextrin, 2 gr sucrose, 0.085 gr CMC, (Sigma, ultra-low viscosity, 36038-4, cas: 9004-32-4), and 14.3 gr TDW were mixed for 10 min at RT until a complete dissolution and acquisition of an aqueous solution. In the next step, 4.165 gr of hemp oil was added to the aqueous phase, homogenized drop ways during homogenization by high shear homogenizer as in Example 1 for the duration of 10 min, followed by sonication as in Example 7.

Droplets size of the O/W nanoemulsion was estimated at Z Average: 145.7 nm peak 1: 30 nm, 4%; peak 2: 100 nm, 49%; peak 3: 307 nm, 47%, Pdi: 0.161; and after dispersion in water at Z Average: 190 nm, peak 1: 180 nm, 94%, peak 2: 963 nm, 3%, peak 3: 5151 nm, 3%, Pdi: 0.322.

It should be noted that among the various selected agents used for the preparation of the various formulations of the invention so far, cyclodextrin was proven to be incompatible in terms of a complete dissolution to obtain the aqueous phase as in Example 1, Stage 1.

Example 11

Preparation of Hemp Oil Powder Tablets for Sublingual Administration

Figure 6:
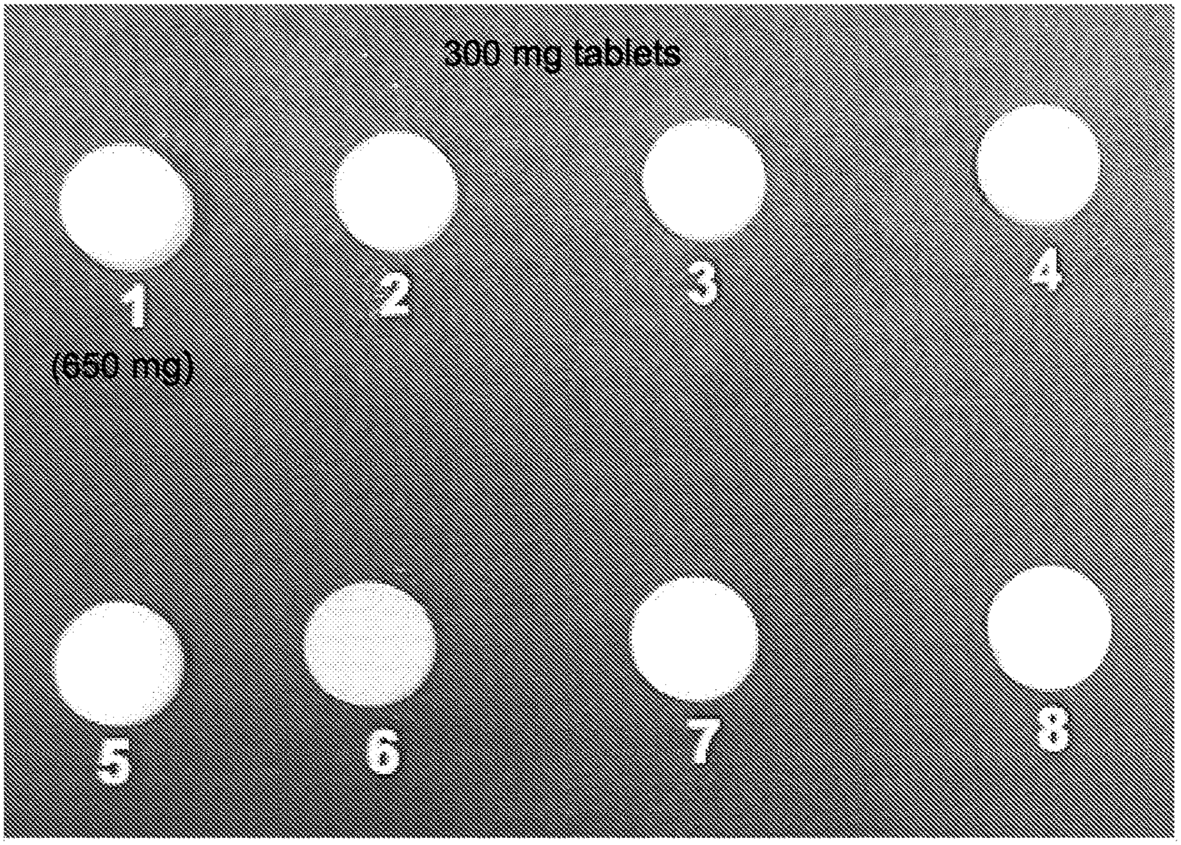
FIG. 6 shows 300 mg and 650 mg tablets containing hemp oil powder (HOP) and additives (magnesium stearate (MS), Glycine (G), PVP (40,000)): Tablets 1=HOP 650 mg; 2=HOP+MS; 3=HOP+G; 4=HOP+PVP; 5=HOP+MS+G; 6=HOP+G+PVP; 7=HOP+PVP+MS; 8=HOP+MS+G+PVP (see Example 11).

The presently described tablets were prepared from the powder obtained in Example 7 using a tablets compressor (PIKE Technologies, CrushIR™, under 9-9.5 tons), certain illustrations thereof are provided in FIG. 6. Each 300 mg or 650 mg tablet contained the hemp oil powder formulation of the invention (HOP), and additional functional agents from state of the art in respective concentrations. One optional application of such tables is for sublingual administration. Certain examples of the produced tablets are given below:

Tablet 1: 300/650 mg of 10.5% hemp oil powder (HOP)
Tablet 2: 294 mg HOP+6 mg Magnesium stearate (MS)
Tablet 3: 294 mg HOP+6 mg Glycine (G)
Tablet 4: 294 mg HOP+6 mg PVP (40,000)
Tablet 5: 288 mg HOP+6 mg MS+6 mg G
Tablet 6: 288 mg HOP+6 mg G+6 mg PVP
Tablet 7: 288 mg HOP+6 mg PVP+6 mg MS
Tablet 8: 282 mg HOP+6 mg MS+6 mg G+6 mg PVP Disintegration tendency of the above types of tablets is shown in Table 4. Tablets were immersed in TDW at 37° C., under gentle shaking. Results of visual inspection are presented (CD—complete dissolution, TNT thin tablet, TKT—thick tablet).

TABLE 4

Disintegration tendency of various tablet preparations

| | Tablet no, | | | | | | | |
|---|---|---|---|---|---|---|---|---|
| Time | 1 | 2 | 3 | 4 | 5 | 6 | 7 | 8 |
| 12 min | TNT | TNT | TNT | TNT | TKT | almost CD | TKT | TKT |
| 15 min | almost CD | TNT | CD | almost CD | TKT | almost CD | TKT | TKT |
| 18 min | almost CD | almost CD | CD | CD | TKT | CD | TKT | TKT |
| 20 min | almost CD | almost CD | CD | CD | TKT | CD | almost CD | TKT |
| 22 min | CD | CD | CD | CD | almost CD | CD | almost CD | TKT |
| 24 min | CD | CD | CD | CD | CD | CD | CD | almost CD |
| 25 min | CD | CD | CD | CD | CD | CD | CD | CD |

The above findings suggest that MS and combination of MS and PVP can inhibit the disintegration of a tablet.

After disintegration, the tablets were subjected to DLS measurements in order to evaluate droplets size, which revealed that for all types of tables the droplets size were still in the nanometric range, e.g., 250-290 nm.

Example 12

Disintegration Profiles of the HOP Tables vs. Centrum Junior Tables

Figure 7:
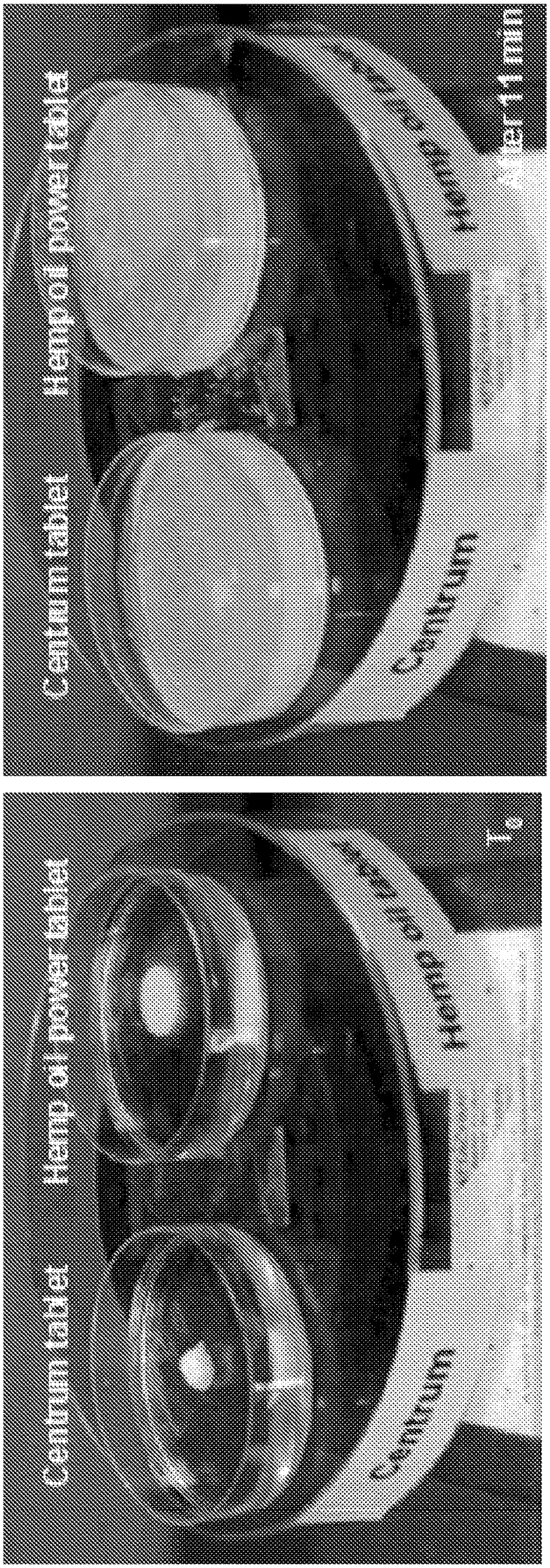
FIG. 7 shows experiments mimicking sublingual dissolution of the HOP and Centrum tablets (see Example 12)

Disintegration profiles of the tablets were further studied comparing HOP table No. 8 (see Example 11) and Centrum Junior sublingual tablet. Both types of tablets, each 300 mg, were immersed in TDW 37° C. under vigorous shaking (see FIG. 7). Tablets were removed from water every 2 min, excess liquid was absorbed into paper, and tablets were weighed.

Figure 8:
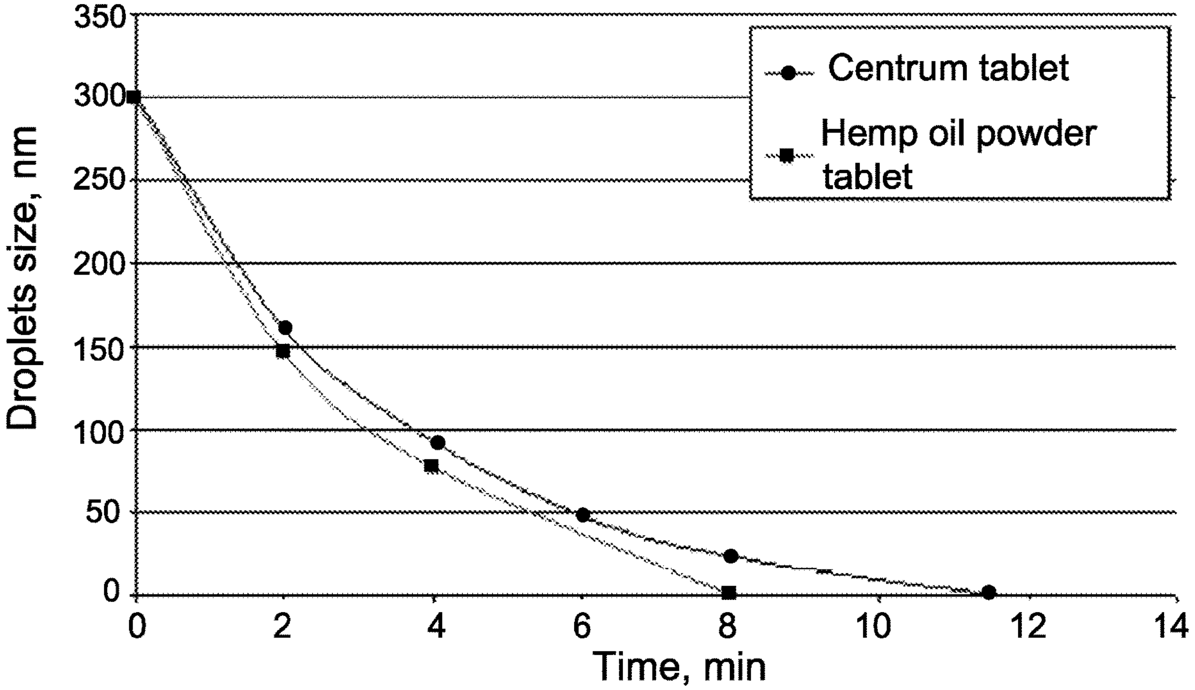
FIG. 8 shows tablet weight vs. disintegration time comparing the HOP (grey squares) and Centrum pill (black dots) tablets.

After 6 min the HOP tablet became very gentle and sensitive to touch, and it was left in water until complete disintegration. The disintegration profile (tablet weight vs. dissolution time) of the HOP tablet was essentially similar to the Centrum tablets (see FIG. 8).

Example 13

The Effect of pH on the Cannabis Oil Emulsion Droplets Size.

In order to evaluate the effect of different pH on the obtained droplets size, three different redispersed emulsions were prepared as follows: 15 mg of cannabis oil powder, (contains 30% oil in powder), were dispersed, by a 20 second of vortex, in 3 ml of aqueous medium to obtain emulsion concentration of 0.5% w/w of the powder in the water.

The pH of the first aqueous medium was 1.2, mimicking stomach conditions. The pH of the second aqueous medium, distilled water, was 5.5 and the pH of the third aqueous medium was 6.8, mimicking intestines conditions.

After redispersion, one droplet of the dispersed emulsion was mixed with 2 ml of the certain aqueous medium and the sample was measured by DLS zetasizer equipment at $T_0$ and after 24 h. Each sample was prepared in duplicate and measured in 3 cycles for each sample.

The average results are presented in Table 5:

TABLE 5

| Size of nanodroplets under various pH values | | | | | | | | |
|---|---|---|---|---|---|---|---|---|
| | avg | pdi | peak1 | % | peak2 | % | peak3 | % |
| T zero | | | | | | | | |
| TDW PH 5.5 | 320 | 0.343 | 307 | 75.6 | 818 | 21.8 | 4972 | 2.6 |
| PH 1.2 | 307 | 0.326 | 467 | 78.8 | 113 | 18.2 | 5319 | 3 |
| PH 6.8 | 376 | 0.423 | 460 | 90 | 67 | 3.3 | 5255 | 6.7 |
| T 24 h | | | | | | | | |
| TDW PH 5.5 | 284 | 0.305 | 257 | 87.8 | 4746 | 12.2 | | |
| PH 1.2 | 312 | 0.376 | 440 | 72.7 | 121 | 24.3 | 5392 | 3 |
| PH 6.8 | 347 | 0.338 | 419 | 79.1 | 106 | 19.9 | 5473 | 1 |

As may be understood from Table 5, the effect of the pH on the droplets size was not significant and also the differences between $T_0$ and after 24 h were negligible.

Example 14

Formulation Comprising Cannabis oil, 19% Oil in Powder. The Final Powder Contains 8 mg THC/gr and 2 mg CBD/gr.

The following exemplary formulation was prepared: 1.44 gr Pluronic F127, 8.5 gr Maltodextrin, 9.6 gr sucrose, one stevia tablet, weigh 82 mg which contains 12 mg of stevia dissolved in 2 gr of worm water and 67 gr TDW were mixed using a magnetic stirrer for 10 min at RT until a complete dissolution. In the next stage, 4.56 gr of the cannabis oil were added to the aqueous phase drop ways during homogenization by high shear homogenizer as in stage III, Example 1. The final emulsion was prepared by HP homogenizer as in Example 7 but with microfluidizer, M110P technology, equipment. Droplet size of the O/W nanoemulsion was estimated at the following values:

For 1 homogenization run: Z Average: 157 nm peak 1: 161 nm, 100%; Pdi: 0.123.

For 2 homogenization runs: Z Average: 158 nm peak 1: 163 nm, 100%; Pdi: 0.103.

For 3 homogenization runs: Z Average: 147 nm peak 1: 148 nm, 100%; Pdi: 0.108.

For 4 homogenization runs: Z Average: 142 nm peak 1: 143 nm, 100%; Pdi: 0.119.

For 5 homogenization runs: Z Average: 141 nm peak 1: 142 nm, 100%; Pdi: 0.112.

The lyophilization step was as in stage V, Example 1. Droplet size after dispersion in water was estimated at Z Average: 224 nm peak 1: 233 nm, 100%, Pdi: 0.194.

The invention claimed is:

1. A water-dispersible powder comprising lipophilic nanospheres having an average diameter between 50 and 900 nm as measured by dynamic light scattering (DLS), the nanospheres comprising a cannabinoid material and having an adsorbed layer comprising at least one solid surfactant, wherein the at least one solid surfactant is ammonium glycyrrhizinate;

the powder further comprising at least one solid cryoprotectant selected from the group consisting of sucrose, trehalose and mannitol, and optionally at least one solid carbohydrate selected from the group consisting of maltodextrin and carboxymethyl cellulose (CMC);

wherein the nanospheres' structure and size is substantially maintained upon dissolution in a water containing environment.

2. The powder according to claim 1, wherein the at least one solid surfactant is ammonium glycyrrhizinate; the at least one solid cryoprotectant is selected from the group consisting of sucrose, trehalose and mannitol; and the at least one solid carbohydrate is selected from the group consisting of maltodextrin and CMC.

3. The powder according to claim 2 comprising combinations of solid surfactants, solid cryoprotectants and solid carbohydrates selected from the following groups: ammonium glycyrrhizinate, sucrose and maltodextrin; or ammonium glycyrrhizinate, mannitol and maltodextrin; or ammonium glycyrrhizinate, trehalose and maltodextrin; or ammonium glycyrrhizinate, sucrose, maltodextrin and CMC; or ammonium glycyrrhizinate, mannitol, maltodextrin and CMC; or ammonium glycyrrhizinate, trehalose, maltodextrin and CMC.

4. The powder according to claim 1, wherein the cannabinoid material comprises at least one synthetic or natural cannabinoid selected from the group consisting of tetrahydrocannabinol, cannabidiol, cannabinol, cannabigerol, cannabichromene, cannabicyclol, cannabivarin, tetrahydrocannabivarin, cannabidivarin, cannabichromevarin, cannabigerovarin, cannabigerol monomethyl ether, a precursor and an acid-form thereof.

5. A method for producing the water-dispersible powder of claim 1, the method comprising:

(i) preparing an initial nanoemulsion by adding an oil phase into an aqueous phase; the aqueous phase comprising the at least one solid cryoprotectant, the at least one solid surfactant and optionally the at least one solid carbohydrate, the oil phase comprising a cannabinoid material comprising at least one synthetic or a natural cannabinoid, a *cannabis* extract or a fraction thereof, (ii) preparing a final nanoemulsion by sonicating or homogenizing the initial nanoemulsion;

(iii) converting the final nanoemulsion to a powder by lyophilization, oven drying or spray drying.

6. A pharmaceutical composition comprising the water-dispersible powder of claim 1, optionally further comprising a pharmaceutically acceptable carrier or excipient.

7. A dosage form for oral or sublingual administration, the dosage form comprising the water-dispersible powder of claim 1.

8. A method of treating a disease or a medical condition related to the beneficial effects of cannabinoids or cannabis, said disease or medical condition being at least one of an inflammatory, a neurological, a psychiatric disorder, a malignancy, an immune disorder, a metabolic disorder, a nutritional deficiency, an infectious disease, and a gastrointestinal disorder, a cardiovascular disorder, a chronic or a neuropathic pain, the method comprising administering to a subject in need thereof a therapeutically effective amount of the water-dispersible powder of claim 1.

9. A nanoemulsion comprising lipophilic nanodroplets of a cannabinoid material and having an average diameter between 50 and 900 nm as measured by DLS; the nanodroplets comprising a solid adsorbed layer comprising at least one soluble solid surfactant of ammonium glycyrrhizinate; at least one soluble solid cryoprotectant selected from the group consisting of sucrose, trehalose and mannitol, and optionally at least one soluble solid carbohydrate selected from the group consisting of maltodextrin and CMC.

10. A dosage form for enteral, parenteral, sublingual, topical or transdermal administrations, the dosage form comprising the water-dispersible powder of claim 1.

11. A dosage form for mucosal, aerosol, inhalation, parenteral, subcutaneous, intravenous, intramuscular, interperitoneal, rectal and vaginal administrations, the dosage form comprising the water-dispersible powder of claim 1.

* * * * *